United States Patent [19]

Reul et al.

[11] Patent Number: 5,663,198
[45] Date of Patent: Sep. 2, 1997

[54] DRUG FORMULATIONS COMPRISING COATED, VERY SPARINGLY WATER-SOLUBLE DRUGS FOR INHALATIONAL PHARMACEUTICAL FORMS, AND PROCESS FOR THEIR PREPARATION

[75] Inventors: Bernhard Reul, Königstein; Walter Petri, Wiesbaden, both of Germany

[73] Assignee: Hoechst Aktiengesellschaft, Frankfurt am Main, Germany

[21] Appl. No.: 274,343

[22] Filed: Jul. 13, 1994

[30] Foreign Application Priority Data

Jul. 15, 1993 [DE] Germany .......... 43 23 636.7

[51] Int. Cl.⁶ .................................. A61K 31/34
[52] U.S. Cl. .............. 514/471; 424/45; 424/46; 424/490; 424/491; 424/494; 424/496; 424/497; 424/499; 424/500
[58] Field of Search ............ 424/45, 46, 490, 424/491, 494, 496, 497, 499, 500; 514/471

[56] References Cited

U.S. PATENT DOCUMENTS 5,230,884  7/1993  Evans et al. .................. 424/45

FOREIGN PATENT DOCUMENTS

| 0 013 376 | 7/1980 | European Pat. Off. ...... C07D 261/18 |
| 0 372 777 B1 | 11/1989 | European Pat. Off. . |
| 0 384 371 A1 | 2/1990 | European Pat. Off. . |
| 0 465 841 A2 | 1/1992 | European Pat. Off. . |
| 0 504 112 A2 | 3/1992 | European Pat. Off. . |
| 4123663A1 | 7/1991 | Germany . |
| WO 90 11754 | 10/1990 | WIPO . |
| WO 91/11173 | 8/1991 | WIPO . |
| WO 92/11496 | 8/1991 | WIPO . |
| WO 91/17748 | 11/1991 | WIPO .......... A61K 31/275 |
| WO 92/00062 | 1/1992 | WIPO . |
| WO 92/02822 | 2/1992 | WIPO .......... G01N 33/68 |
| WO 92 08446 | 5/1992 | WIPO . |
| WO 92/08447 | 5/1992 | WIPO . |
| WO 92/16226 | 10/1992 | WIPO .......... A61K 37/02 |

OTHER PUBLICATIONS

Karl, Thoma, "Aerosole"; pp. 154–160; Frankfurt/Main (1987).
European Search Report dated Jul. 15, 1994.
Glant et al., *Immunopharmacology*, 23, 1992, pp. 105–116.
Zielinski et al., *Immunobiology*, 186(1–2), 1992, p. 113.
Bartlett et al., *Agents and Actions*, 32(1/2), 1991, pp. 10–21.
Zielinski et al., *Agents Actions*, 38, 1993, pp. C80–C82.
Mattar et al., *FEBS Letters*, 334(2), 1993, pp. 161–164.

*Primary Examiner*—Brian M. Burn
*Attorney, Agent, or Firm*—Finnegan, Henderson, Farabow, Garrett & Dunner, L.L.P.

[57] ABSTRACT

Drug formulations comprising coated, very sparingly water-soluble drugs for inhalational pharmaceutical forms, and process for their preparation.

Drug formulations comprising micronized particles of very sparingly water-soluble drugs which are coated with a natural, physiologically acceptable ampholytic surfactant soluble in water to give a micellar/colloidal solution, and a process for the preparation of these drug formulations, are described. When placed in an appropriate final container and after the addition of a chlorine-free, partially fluorinated propellant gas liquefiable under pressure, these formulations are suitable for inhalation.

14 Claims, No Drawings

DRUG FORMULATIONS COMPRISING COATED, VERY SPARINGLY WATER-SOLUBLE DRUGS FOR INHALATIONAL PHARMACEUTICAL FORMS, AND PROCESS FOR THEIR PREPARATION

The invention relates to drug formulations comprising one or more very sparingly water-soluble, micronized drugs which is/are lyophilized or spray-dried together with a special ampholytic surfactant soluble in water to give a micellar/colloidal solution.

The drugs coated in this way, dosed into final containers, optionally with the addition of propellant gas liquefiable under pressure, are suitable as an inhalational pharmaceutical form.

Drug formulations of very sparingly water-soluble drugs, suitable for inhalation, are described.

Thus EP-A-0 465 841 relates to quick-acting inhalational pharmaceutical forms of the very sparingly water-soluble furosemide or piretanide.

The powder inhalant (=DPI) described in said patent application has a poor local tolerance; the low wettability of the very sparingly water-soluble drugs causes irritation on the pulmonary mucosa (cf. Karl Thoma, Aerosols (Aerosols), Frankfurt/Main, 1979, page 154–160).

In addition, the high proportions of adjunct (up to 50% of lactose), which are absolutely essential for reducing the known adhesion and agglomeration properties of very sparingly water-soluble, micronized drugs, exacerbate the irritation phenomena on the pulmonary mucosa.

The controlled-dosage aerosol (=MDI) also described in EP-A-0 465 841 is a suspension aerosol and has the following disadvantages:

1. the propellant gas mixture liquefiable under pressure, used as propellant, is based purely on CFCs, i.e. its future use will be banned by the new legislation,
2. the physiologically acceptable suspension aids used, which have surface-active properties and are soluble in the CFC base, such as oleic acid, benzalkonium chloride, lecithin and sorbitan trioleate, are sparingly soluble or insoluble in the chlorine-free, partially fluorinated hydrocarbons liquefiable under pressure (=HFCs) which are to be permissible in the future, i.e. they can no longer be used in the future if the conventional preparative processes are to be retained.

Apart from those mentioned under 2., the literature describes other surface-active substances which dissolve in the HFC medium as suspension aids for controlled-dosage suspension aerosol formulations (cf. e.g. WO 91/11173, WO 92/00062 and EP-A-0 504 112).

Because their inhalation toxicity is still unknown, these other surface-active substances are not yet permitted for inhalational pharmaceutical forms.

The literature further describes a process for the coating of certain drugs with the hitherto conventional suspension aids oleic acid, benzalkonium chloride, lecithin and sorbitan trioleate, and the use of the coated drugs in controlled-dosage suspension aerosol formulations based on CFCs or HFCs (cf. WO 92/08447), optionally with ethanol as cosolvent (cf. WO 92/08446).

For physical reasons, however, the process described in said patent documents is not suitable for the uniform, continuous and constant-weight coating of each individual micronized drug particle; the evaporation of the solvent inevitably produces a chromatography effect, which leads not only to the formation of drug particles coated to different thicknesses, but also to coarsening of the particles as a result of conglutination.

Furthermore, it is only possible to coat drugs which are very sparingly soluble or have a limited solubility in the non-polar solvents described, e.g. isopentane and trichlorofluoromethane, i.e. preferably hydrophilic drugs.

Equally, it is only possible to use adjuncts which are soluble in the solvents described, i.e. preferably lipophilic adjuncts.

The literature also describes the use of chlorine-free, partially fluorinated hydrocarbons liquefiable under pressure (=HFCs), e.g. heptafluoropropane (1,1,1,2,3, 3,3-heptafluoropropane, R 227) or tetrafluoroethane (1,1,1,2-tetrafluoroethane, R 134a), as propellants for industrial and cosmetic aerosols (cf. EP-A-0 384 371) as well as for pharmaceutical aerosols (cf. EP-B-0 372 777), optionally mixed with halogen-free hydrocarbons (cf. WO 91/11496) or mixed with ethanol (cf. DE-A-41 23 663).

The object of the invention was:

a. to improve the known poor tolerance of very sparingly water-soluble drugs which are not easily wettable on the pulmonary mucosa and which therefore cause irritation, b. to formulate inhalational pharmaceutical forms with very sparingly water-soluble drugs in the form of powder inhalants or controlled-dosage suspension aerosols with the chlorine-free, partially fluorinated propellant gas liquefiable under pressure (R 227), and c. to minimize the substance loading in the lung caused by formulation constituents.

This object is achieved by the discovery of a solid stable combination comprising very sparingly water-soluble, micronized drug and a natural ampholytic surfactant soluble in water to give a micellar/colloidal solution. This combination is also referred to hereafter as a drug/adjunct pair (=DAP).

An ampholytic surfactant is a natural, physiologically acceptable ampholyte soluble in water to give a micellar/colloidal solution and is analogous to the endogenous surfactant (cf. Ernst Mutschler, Arzneimittelwirkungen (Drug Actions), 6th edition, Stuttgart, 1991, and Wolf-Dieter Keidel, Physiologie (Physiology), 6th edition, Stuttgart-New York, 1988).

Soluble to give a micellar/colloidal solution means that the ampholyte forms both micelles and colloids (0.1 to 500 nm).

Micronized drug means that its particle size is suitable for inhalation, i.e. smaller than 5 μm.

The invention therefore relates to a drug formulation comprising a very sparingly water-soluble, micronized drug or a very sparingly water-soluble, micronized drug mixture, wherein the drug or the drug mixture is coated with a natural, physiologically acceptable ampholytic surfactant soluble in water to give a micellar/colloidal solution.

The invention further relates to a process for the preparation of the DAP, i.e. coating of the drug or drug mixture, which comprises suspending the very sparingly water-soluble, micronized drug or drug mixture in the aqueous micellar/colloidal solution of the ampholytic surfactant and then spray-drying or lyophilizing the suspension.

In the carrying-out of the process according to the invention, the very sparingly water-soluble drug or drug mixture is micronized by conventional methods, e.g. precipitation and grinding.

Drying by lyophilization is preferred.

The solid stable DAP according to the invention is suitable for inhalation, possible pharmaceutical forms being both the powder inhalant (=DPI) and the controlled-dosage aerosol (=MDI).

The invention therefore also relates to these pharmaceutical forms, the DAP conveniently being filled into containers suitable for powder inhalant, e.g. into a capsule such as a gelatin capsule, or into a cartridge for multiple-dosage systems, or into containers suitable for controlled-dosage aerosols, with the addition of a propellant gas liquefiable under pressure.

Propellant gases used for the pharmaceutical form of the controlled-dosage aerosol are those which do not harm the ozone layer, i.e. chlorine-free, partially fluorinated hydrocarbons liquefiable under pressure (HFCs), such as 1,1,1,2,3,3,3-heptafluoropropane (=R 227) and 1,1,1,2-tetrafluoroethane (=R 134a) or a mixture thereof.

Special phospholipid mixtures with a phosphatidylcholine content of 20–95%, preferably 40–80%, soluble in water to give a micellar/colloidal solution, are used as the ampholytic surfactant.

Depending on the drug type used and the dosage, and depending on the chosen pharmaceutical form, different ampholytic surfactant types (i.e. with different phosphatidylcholine contents) and concentrations are required for the optimal DAP in each case.

By adapting in each individual case, the content of ampholytic surfactant in the DAP varies between 0.01 and 10%.

Possible drugs are any substances suitable for inhalation which are very sparingly water-soluble (solubility in water less than 0.014):

e.g.

as diuretics: furosemide, azosemide, piretanide, bumetanide and torasemide as antimycotics: clotrimazole, miconazole, ketoconazole, itraconazole, bifonazole and rilopirox as antidiabetics: glibenclamid, glimepirid and insulin as antiallergics: ASS/furosemide combination The lyophilization process gives the hydrophobic surface of the very sparingly water-soluble, micronized drug particles a uniform hydrophilic coating, thereby eliminating the known adhesion and agglomeration properties of micronized drug particles.

The use of a special natural phospholipid mixture (ampholytic surfactant) which is chemically almost identical to the surfactant formed by the body and present on the pulmonary mucosa, achieves not only the good local tolerance but also an outstanding wettability, thus avoiding the known irritant effects.

The DAP prepared and formulated in this way is particularly suitable for use in the inhalational pharmaceutical forms of the powder inhalant and the controlled-dosage aerosol with the propellant gases R 227 and R 134a. The formulations do not require any other flow-improving or suspension-stabilizing adjuncts, so the substance loading of the lung is extremely small.

These DAP formulations are pharmaceutically perfect, can be administered in accurate doses and are stable on storage.

The invention will now be illustrated further by means of the following Examples:

EXAMPLE 1

Preparation of drug/adjunct pair (DAP)

0.4 g of phospholipid mixture (80% of phosphatidylcholine) is dispersed in 80.0 ml of water for injectable preparations, for 24 hours at laboratory temperature (ca. 23° C.), with rotation. 20.0 g of micronized furosemide (particle size 98%<5µ) are introduced into and suspended in the slightly opalescent, micellar/colloidal phospholipid solution formed above. The homogeneous air-free suspension is frozen by the shock process (ca. −80° C.) and then dried for 48 hours under high vacuum (13 Pa) at laboratory temperature.

Yield: 19.2 g.

The DAP is obtained in the form of a loose, free-flowing powder with a phosphatidylcholine content of 1.6% and a water content of <0.1%. The active ingredient content is 97–98%.

EXAMPLE 2

Preparation of DAP powder inhalant

The DAP (composition according to Example 1) is passed through a sieve (mesh size 0.315 mm) and filled into size 2 hard gelatin capsules at a rate of 20.4 mg in each, corresponding to 20.0 mg of furosemide.

The PAP can be administered perfectly by means of a suitable commercial applicator (e.g. "Spinhaler"). The properties in respect of application technology satisfy the conventional pharmaceutical requirements.

EXAMPLE 3

Preparation of DAP controlled-dosage aerosol Method A

The DAP (composition according to Example 1) is passed through a sieve (mesh size 0.315 mm) and filled into containers suitable for controlled-dosage aerosols (integral aluminium can, volume 22 ml) at a rate of 0.510 g of DAP in each, the containers are sealed with a metering valve suitable for controlled-dosage suspension aerosols, and each container is then filled with 13.49 g of R 227 through the metering valve. A homogeneous stable suspension of DAP in R 227 is produced after brief shaking or after ultrasound treatment.

EXAMPLE 4

Preparation of DAP controlled-dosage aerosol Method B 0.715 kg of DAP (composition according to Example 1) is placed in a pressurized vessel (volume 20 l) equipped with a stirrer and a homogenizer, and 7.985 kg of R 227 are then added under pressure. The whole is homogenized to form a suspension. Containers suitable for controlled-dosage aerosols (integral aluminium cans, volume 22 ml) are sealed empty with a metering valve (volume 0.1 ml) suitable for controlled-dosage suspension aerosols. In the first filling process, 12.5 g of the homogeneous suspension are metered into each container by the known pressure-filling technique. In the second filling process which follows, the contents of each container are diluted with 1.5 g of R 227 in order to flush out the metering valves.

One dose of the controlled-dosage suspension aerosol prepared by method A or B contains, per puff (0.1 ml), 5.1 mg of DAP (composition according to Example 1), corresponding to 5.0 mg of furosemide, 0.1 mg of phosphatidylcholine and 134.9 mg of R 227.

EXAMPLE 5

Preparation of DAP 0.3 g of phospholipid mixture (45% of phosphatidylcholine) is dispersed in 270.0 ml of water for injectable preparations, for 24 hours at laboratory temperature (ca. 23° C.), with rotation. 30.0 g of micronized rilopirox (particle size 98%<5 µ) are introduced into and suspended in the micellar/colloidal phospholipid solution formed above.

The homogeneous air-free suspension is frozen by the shock process (ca. −80° C.) and then dried for 48 hours under high vacuum (13 Pa) at laboratory temperature.

Yield: 29.1 g.

The DAP is obtained in the form of a loose, free-flowing powder with a phosphatidylcholine content of 0.5% and a water content of 0.1%. The active ingredient content is 98–99%.

EXAMPLE 6

DAP controlled-dosage aerosol

The DAP (composition according to Example 5) is passed through a sieve (mesh size 0.315 mm) and filled into containers suitable for controlled-dosage aerosols (integral aluminium can, volume 22 ml) at a rate of 0.404 g of DAP in each, the containers are sealed with a metering valve suitable for controlled-dosage suspension aerosols, and 27.60 g of R 227 are then filled into each container through the metering valve. A homogeneous stable suspension of DAP in R 227 is produced after brief shaking or after ultrasound treatment.

We claim:

1. A drug formulation comprising a chlorine-free, partially fluorinated hydrocarbon formulated with micronized particles of a very sparingly water-soluble drug that are sufficiently coated with a natural, physiologically acceptable ampholytic phospholipid surfactant that is soluble in water to give a micellar/colloidal solution.

2. A drug formulation as claimed in claim 1, wherein the drug is coated with a phospholipid mixture having a phosphatidylcholine content of 20–95%.

3. A process for the preparation of a drug formulation as claimed in claim 1 or 2, which comprises the steps of suspending the micronized drug in an aqueous micellar/colloidal solution of the ampholytic phospholipid mixture surfactant and spray-drying or lyophilizing the suspension.

4. An aerosol which contains a drug formulation comprising micronized particles of a very sparingly water-soluble drug which are coated with a natural, physiologically acceptable ampholytic phospholipid surfactant mixture that is soluble in water to give a micellar/colloidal solution and a chlorine-free, partially fluorinated propellant gas liquefiable under pressure selected from the group consisting of heptafluoropropane (R 227), tetrafluoroethane (R 134a) and a mixture thereof, said aerosol being free of any other flow improving or suspension-stablilizing adjunct.

5. A process for the preparation of an aerosol as claimed in claim 4, comprising the steps of
  a. dosing the drug formulation into an appropriate container; sealing the container with a metering valve and adding an amount of chlorine-free propellant gas required to form the aerosol, or
  b. preparing the aerosol from the drug formulation in a separate, pressure-resistant first container homogenizing the aerosol and filling the homogenized aerosol into a second container.

6. A process for the production of an aerosol, which comprises filling the drug formulation as claimed in claim 1 into a suitable capsule or reservoir system.

7. A drug formulation as claimed in claim 1 which contains a diuretic.

8. A drug formulation as claimed in claim 1 which contains furosemide.

9. A drug formulation as claimed in claim 1 which contains an antidiabetic.

10. A drug formulation as claimed in claim 1 which contains an antimycotic.

11. A drug formulation as claimed in claim 1 which contains rilopirox.

12. A drug formulation as claimed in claim 2 wherein the phosphatidylcholine content is 40–80%.

13. An aerosol which contains a drug formulation as claimed in claim 2 wherein said chlorine-free, partially fluorinated hydrocarbon is a propellant gas liquefiable under pressure.

14. An aerosol as claimed in claim 13, wherein the chlorine-free, partially fluorinated propellant gas liquefiable under pressure is heptafluoropropane (R 227) or tetrafluoroethane (R 134a) or a mixture of these two substances.

* * * * *